US011241547B2

(12) United States Patent
Denton et al.

(10) Patent No.: US 11,241,547 B2
(45) Date of Patent: Feb. 8, 2022

(54) ATOMIZER FOR NASAL THERAPY

(75) Inventors: Marshall T. Denton, Salt Lake City, UT (US); Perry W. Croll, Salt Lake City, UT (US); Mark A. Christensen, Salt Lake City, UT (US); Timothy R. Wolfe, Salt Lake City, UT (US); J. Michael Brown, Salt Lake City, UT (US)

(73) Assignee: TELFLEX MEDICAL INCORPORATED, Wayne, PA (US)

( * ) Notice: Subject to any disclaimer, the term of this patent is extended or adjusted under 35 U.S.C. 154(b) by 554 days.

(21) Appl. No.: 13/884,576

(22) PCT Filed: Nov. 11, 2011

(86) PCT No.: PCT/IB2011/002809
§ 371 (c)(1),
(2), (4) Date: Aug. 2, 2013

(87) PCT Pub. No.: WO2012/063124
PCT Pub. Date: May 18, 2012

(65) Prior Publication Data
US 2013/0298902 A1    Nov. 14, 2013

Related U.S. Application Data

(60) Provisional application No. 61/456,780, filed on Nov. 12, 2010.

(51) Int. Cl.
*A61M 11/00* (2006.01)
*A61M 15/08* (2006.01)
(Continued)

(52) U.S. Cl.
CPC ........... *A61M 11/00* (2013.01); *A61M 11/007* (2014.02); *A61M 11/06* (2013.01);
(Continued)

(58) Field of Classification Search
CPC .... A61M 11/06; A61M 15/08; A61M 11/007; A61M 1/0039; A61M 1/0001;
(Continued)

(56) References Cited

U.S. PATENT DOCUMENTS 2,096,831 A    10/1937  Wappler
2,252,874 A     8/1941  Vischer, Jr.
(Continued)

FOREIGN PATENT DOCUMENTS

CN    1166138 A    11/1997
CN    2579352 Y    10/2003
(Continued)

OTHER PUBLICATIONS

International Search Report; PCT/IB2011/002809 dated Mar. 7, 2012.

*Primary Examiner* — Elliot S Ruddie
(74) *Attorney, Agent, or Firm* — BakerHostetler

(57) ABSTRACT

An atomizing nozzle structured particularly for nasal therapy. Preferred embodiments include a 2-piece atomizing nozzle structured to couple with luer-locking structure carried by a syringe. Such an atomizing nozzle includes a nasal stopper and a stem. A preferred nasal stopper includes a distal tip sized for insertion into a nostril of a human child, with a proximal shield portion being structured to resist over-insertion of a discharge orifice into the nostril. A nasal stopper desirably provides a centering function to urge the discharge orifice away from a nasal wall. One operable stem is structured to couple with the stopper and desirably carries unitary thread structure at a proximal end. A second operable stem is structured as a unitary part of the nasal stopper and also desirably carries unitary thread structure at a proximal end. Certain embodiments may also include spacer structure configured to reduce a dead volume inside the atomizing nozzle. Other embodiments may also include spacer struc-
(Continued)

ture configured to reduce dead volume inside a syringe that is coupled to the atomizing nozzle.

13 Claims, 13 Drawing Sheets

(51) Int. Cl.
*A61M 11/06* (2006.01)
*B05B 11/02* (2006.01)
*B05B 1/34* (2006.01)

(52) U.S. Cl.
CPC ........... *A61M 15/08* (2013.01); *B05B 1/3436* (2013.01); *B05B 11/02* (2013.01); *A61M 11/001* (2014.02)

(58) Field of Classification Search
CPC ................ A61M 1/0066; A61M 1/008; A61M 2205/10; A61M 2210/0618; A61M 2025/0233; A61M 15/085; A61M 16/0666–0672; A61M 11/00–002; A61M 11/006–008; A61M 11/04; B05B 1/343; B05B 11/02; B05B 1/34–3457; A62B 23/06
USPC ............ 128/200.14, 200.22, 200.23, 202.27, 128/207.14, 200.18, 200.21; 604/187, 604/239, 257, 275, 278
See application file for complete search history.

(56) References Cited

U.S. PATENT DOCUMENTS

| | | | | |
|---|---|---|---|---|
| 3,124,959 | A | 3/1964 | Pall et al. | |
| 4,096,759 | A | 6/1978 | Desor | |
| 4,256,099 | A | 3/1981 | Dryden | |
| 4,445,366 | A | 5/1984 | Gray | |
| 4,923,448 | A * | 5/1990 | Ennis, III | A61M 5/31 128/200.14 |
| 5,237,988 | A | 8/1993 | McNeese | |
| 5,241,956 | A | 9/1993 | Brain | |
| 5,328,099 | A * | 7/1994 | Petit | A61M 11/02 128/200.14 |
| 5,429,600 | A * | 7/1995 | Heinke | A61D 7/00 604/192 |
| 5,609,581 | A * | 3/1997 | Fletcher | A61J 1/067 401/132 |
| 5,899,878 | A * | 5/1999 | Glassman | A61M 3/0279 433/95 |
| 5,935,084 | A | 8/1999 | Southworth | |
| 6,079,409 | A | 6/2000 | Brain | |
| 6,112,743 | A * | 9/2000 | Denton | A61M 11/06 128/200.14 |
| 6,626,379 | B1 * | 9/2003 | Ritsche | B05B 11/0078 239/303 |
| 6,698,429 | B2 | 3/2004 | Croll et al. | |
| 7,296,566 | B2 * | 11/2007 | Alohas | A61M 15/08 128/200.14 |
| 7,895,497 | B2 | 2/2011 | Pisek et al. | |
| 2002/0026178 | A1 | 2/2002 | Ouchi | |
| 2002/0174865 | A1 * | 11/2002 | Gatton, Jr. | A61M 15/0028 128/200.18 |
| 2004/0089307 | A1 | 5/2004 | Brain | |
| 2005/0066975 | A1 | 3/2005 | Brain | |
| 2005/0081861 | A1 | 4/2005 | Nasir | |
| 2005/0131357 | A1 | 6/2005 | Denton | |
| 2006/0162722 | A1 * | 7/2006 | Boehm | A61M 11/06 128/200.14 |
| 2006/0180156 | A1 | 8/2006 | Baska | |
| 2006/0201516 | A1 | 9/2006 | Petersen et al. | |
| 2008/0041392 | A1 | 2/2008 | Cook | |
| 2008/0276936 | A1 | 11/2008 | Cook | |
| 2011/0226256 | A1 | 9/2011 | Dubach | |
| 2011/0245805 | A1 | 10/2011 | Swinehart et al. | |
| 2012/0199119 | A1 * | 8/2012 | Pardonge | B05B 11/0005 128/200.22 |

FOREIGN PATENT DOCUMENTS

| | | | | |
|---|---|---|---|---|
| CN | 1863568 | A | 11/2006 | |
| CN | 2882657 | Y | 3/2007 | |
| CN | 101057994 | A | 10/2007 | |
| CN | 100531818 | C | 8/2009 | |
| CN | 201516220 | U | 6/2010 | |
| CN | 201684261 | U | 12/2010 | |
| CN | 101991898 | A | 3/2011 | |
| CN | 103221087 | B | 7/2013 | |
| DE | 2945662 | A1 | 5/1981 | |
| EP | 0 389 272 | | 9/1990 | |
| EP | 1 800 706 | | 6/2007 | |
| FR | WO 2011048332 | A1 * | 4/2011 | B05B 11/0005 |
| GB | 2454199 | A | 5/2009 | |
| GB | 2436294 | B | 12/2009 | |
| JP | H08-547 | A | 1/1996 | |
| JP | H09-505211 | A | 5/1997 | |
| JP | H10-179745 | A | 7/1998 | |
| JP | 2003-511108 | A | 3/2003 | |
| JP | 2006-522623 | A | 10/2006 | |
| JP | 2008-526393 | A | 7/2008 | |
| TW | 200706196 | A | 2/2007 | |
| WO | WO 00/20062 | | 4/2000 | |
| WO | WO 06/037626 | | 4/2006 | |
| WO | WO 06/125986 | | 11/2006 | |
| WO | WO 07/131267 | | 11/2007 | |
| WO | WO 09/156949 | | 12/2009 | |
| WO | WO 10/060224 | | 6/2010 | |
| WO | WO 10/100419 | | 9/2010 | |
| WO | 2012063124 | | 5/2012 | |
| WO | WO 13/066195 | | 5/2013 | |

* cited by examiner

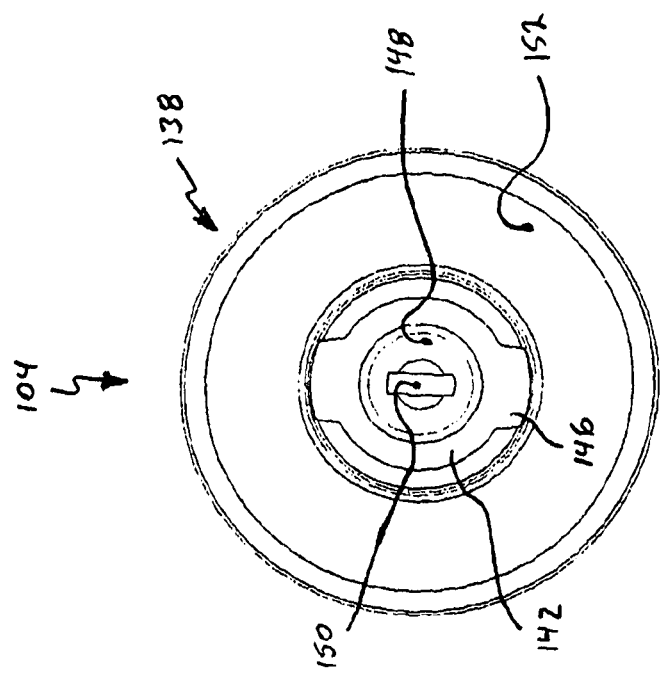
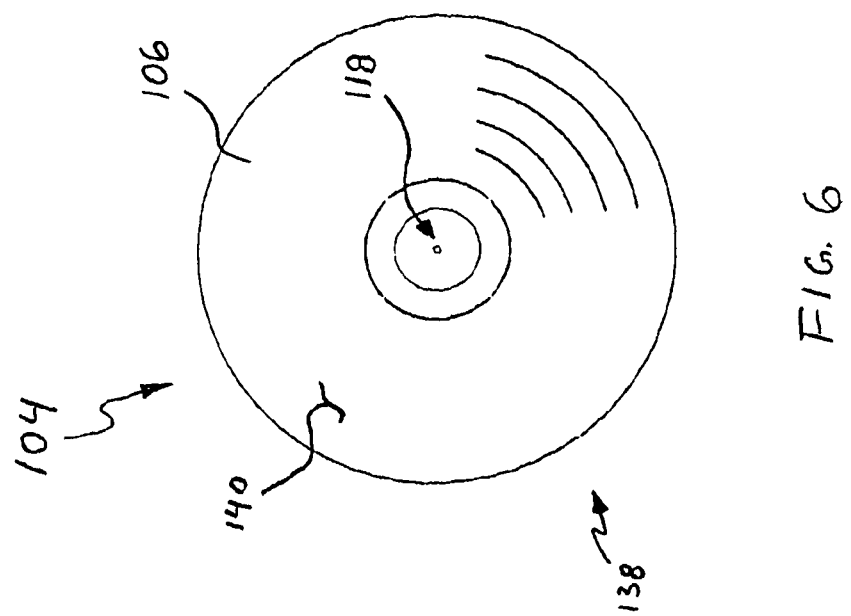
FIG. 7
FIG. 6

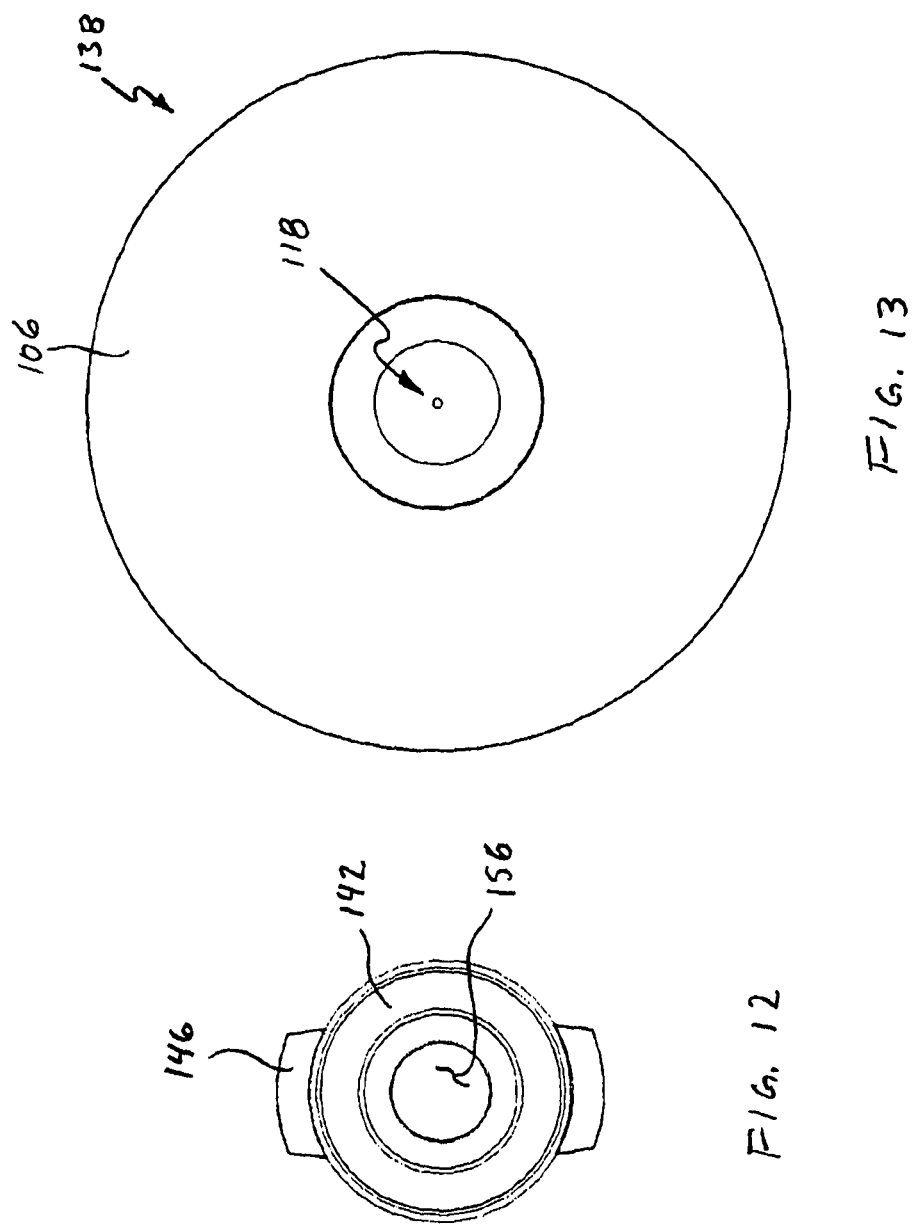

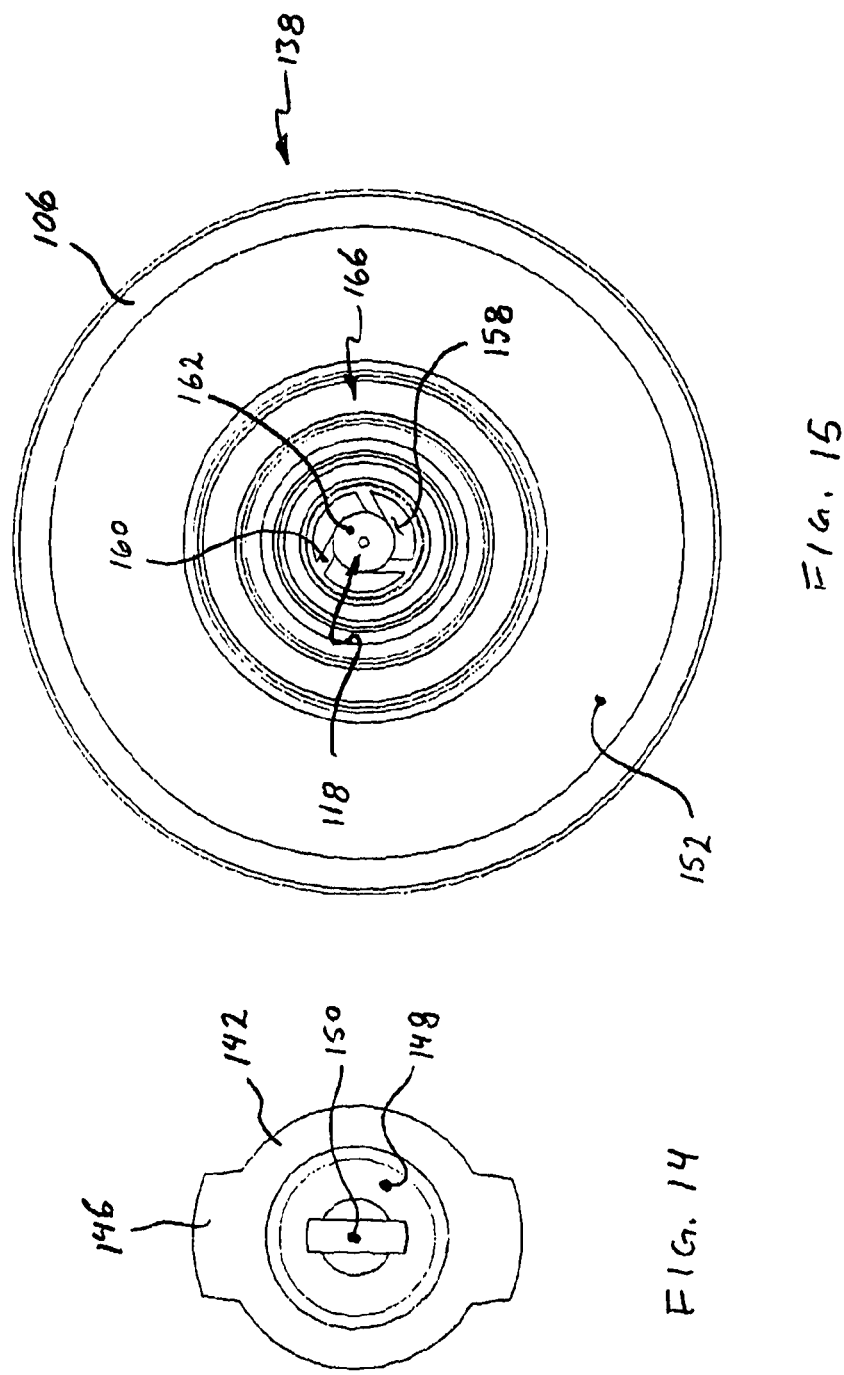

ATOMIZER FOR NASAL THERAPY

CROSS-REFERENCE TO RELATED APPLICATION(S)

This application is a national phase entry under 35 U.S.C. § 371 of international Patent Application PCT/IB2011/002809, filed Nov. 11, 2011, designating the United States of America and published in English as International Patent Publication WO2012/063124 A1 on May 18, 2012, which claims the benefit under Article 8 of the Patent Cooperation Treaty and 35 U.S.C. § 119(e) to U.S. Provisional Patent Application Ser. No. 61/456,780, filed Nov. 12, 2010.

TECHNICAL FIELD

The invention relates to atomizing nozzles and devices which dispense treatment fluids in a misted or dispersed, small particle size, form and to methods of their manufacture and use. Certain devices constructed according to the invention are particularly suitable for use in nasal therapy.

BACKGROUND

Details of the principles of operation and construction of certain operable atomizing nozzles are disclosed in U.S. Pat. No. 6,698,429, titled "MEDICAL ATOMIZER", issued Mar. 2, 2004, to Perry W. Croll, et al., the entire disclosure of which is hereby incorporated as though set forth herein in its entirety. The principal focus of the '429 patent provides atomizing nozzles that may be inserted into, and advanced along the length of, conduit passages having cross-section areas of relatively small size.

One commercially available device commonly used for dispensing treatment fluid in substantially misted form includes the widely used white polypropylene actuator 50 illustrated in FIG. 1. Such actuator is manufactured by a company known as Valois or Aptar and having a worldwide presence. The actuator is typically provided as an OEM component and is ubiquitously available in an assortment of spray-bottle, or pump-bottle applications. Although certain atomizing details are approximated or not illustrated, relevant external structure of the actuator 50 is illustrated substantially true to scale.

Actuator 50 is exemplary of a discharge nozzle that is expressly not structured to resist over-insertion of the distal end into a nostril when applying topical therapy to nasal passages. In fact, the gradual taper and relatively small diameter of the extended discharge nozzle can easily permit over-insertion in an adult nostril. The conic angle γ calculated using direct measurements of a purchased actuator is about 3-½ degrees, and the nozzle tip is located more than 1 inch from the oblong cantilevered trigger structure 52 on which a user's fingers rest to actuate a fluid-dispensing pump bottle. The tip diameter 54 is about 0.3 inches, and the diameter 56 at the interference ring is about 0.41 inches. The interference ring is spaced apart from the tip by about 0.9 inches. Such slender, and small diameter, protruding structure can easily be over-inserted into an adult nostril, and cause damage to sensitive nasal tissue.

Actuator 50 is also exemplary of a commercially available 2-piece atomizing nozzle. The internal distal surface of bore 58 is believed to carry turbine structure effective to apply a spin to fluid prior to expelling the fluid through a discharge orifice. A core element (not illustrated) forms a proximal surface for a turbine chamber. The core element is installed in a press-fit inside bore 58. Fluid is believed to flow distally along the side of the solid core element to the turbine chamber. A fluid supply conduit from a pump bottle can be placed in fluid communication with the proximal end of bore 58 (typically with a press-fit installation), to introduce treatment fluid to bore 58.

An exemplary 6-piece atomizer assembly adapted for use in nasal therapy is generally indicated at 60 in FIG. 1A. Such atomizer assembly is commercially available under part name MAD Nasal, MAD 300 from Wolfe Tory Medical, Inc., having a place of business located at 79 West 4500 South, Suite 18, Salt Lake City, Utah 84107. Atomizer assembly 60 includes atomizing nozzle, generally 62, affixed to a short extension conduit 64. A malleable wire is installed in one of two lumen that extend lengthwise through the conduit. A separate fluid guidance structure (not illustrated) is trapped inside the nozzle tip shell upon assembly of the nozzle tip shell and extension conduit. Luer-locking structure, generally 66, including torsion wings 68 and thread 70, is affixed to the proximal end of conduit 64. The nozzle 62 and extension conduit 64 are forced into a soft rubber nasal stopper 72.

It would be an improvement to provide a 2-piece atomizer having integral structure of a discharge tip configured to permit insertion of a distal tip end into even a child's nostril, and to resist over-insertion of the tip end into other nostrils having a range in larger size. A further advance would provide a 2-piece atomizer including integral threaded luer connection structure. Another advance would provide an atomizing nozzle having a minimized dead volume to promote efficient use, and reduce waste, of treatment fluids.

BRIEF SUMMARY

Provided is an operable atomizing nozzle that can be formed from only two pieces: a nasal stopper, and a stem. That is, a combination consisting of only the stem and the nasal stopper is operable as an atomizing nozzle. The atomizing nozzle is typically structured for use in combination with a syringe.

Desirably, a distal end of the nasal stopper includes a protruding tip that carries a discharge orifice for dispensing treatment fluids in misted, or atomized, form. A preferred such tip is sufficiently small in cross-section as to permit entrance of the tip into a nostril opening of a human child. Desirably, the leading end of the tip is structured to be blunt to avoid causing tissue damage inside a nostril. Also, the trailing end of a tip is typically structured to suggest a cylindrical section, a length of the cylindrical section being sized to form an interference with structure of a nostril to resist transverse displacement of the tip from an inserted position inside the nostril.

A proximal portion of the nasal stopper is typically configured to resist over-insertion of the protruding tip into a child's nostril opening. A currently preferred nasal stopper consists of a single unitary element. A currently preferred proximal portion may be characterized as a shield affixed to the protruding tip and arranged to define a flaring wall providing a variable diameter sized to contact skin around the opening of a plurality of different-sized nostrils effective to resist over-insertion of the distal portion of the nasal stopper. One workable shield includes a substantially conic surface, the conic angle being selected from a range between about 20 degrees and about 60 degrees. The currently preferred conic angle is about 30 degrees. A desirable shield comprises a substantially conic distally facing surface devoid of radial protrusions, with the proximal end of the conic surface being configured as a cantilevered free end.

A workable stem extends in a length direction between a proximal end and a distal end and is configured to couple directly to the nasal stopper. The stem provides a lumen to conduct treatment fluid to the atomizing structure. A preferred stem consists of a single unitary element. Integral thread structure carried at the proximal end of the stem is typically configured to couple with a lure-locking portion of a syringe. Sometimes, the stem is sized in length such that, upon assembly of the atomizer, that thread structure is disposed inside a volume defined by the nasal stopper. A preferred stem is structured to require fluid to discharge in a radial direction from at least one side discharge opening disposed at a location proximal to the distal end of the stem.

A workable connection may be formed between a stem and a nasal stopper between first cooperating coupling structure configured to form a primary distal fluid seal to resist leakage of fluid from the lumen. A workable connection between a stem and nasal stopper may also include a second cooperating coupling structure configured to form a primary torsion-carrying connection.

The combination formed by the nasal stopper and stem forms an atomizer including the aforementioned discharge orifice. That is, the discharge orifice is disposed in a wetted fluid path to conduct fluid from a turbine chamber of the atomizer. The stem is structured to provide a lumen for communication of treatment fluid to the turbine chamber for discharge of treatment fluid substantially as a mist from the discharge opening. A portion of the proximal wall of the turbine chamber is defined by structure disposed at a distal end of the stem.

Sometimes, a filler piece may be installed within the lumen of the stem. A workable filler piece is structured to reduce dead volume inside the working portion of the atomizer, itself, to less than about 0.02 ml. An alternative workable filler piece is further structured to reduce dead volume inside a syringe that is connected to the atomizer assembly to the extent that the dead volume of the combination including the syringe and atomizer is less than about 0.03 ml. In more preferred embodiments, the dead volume in a combination including a syringe and atomizer is less than 0.02 ml. In even more highly preferred embodiments, the dead volume in a combination including a syringe and atomizer is less than about 0.01 ml.

The inventions includes a method of, e.g., nasal, or other delivery comprising utilizing the described atomizing nozzle.

BRIEF DESCRIPTION OF THE DRAWINGS

In the drawings, which illustrate what are currently regarded as the best modes for carrying out the invention:

FIG. 6 is a top view of the atomizer assembly illustrated in FIG. 2;

FIG. 7 is a bottom view of the atomizer assembly illustrated in FIG. 2;

FIG. 12 is a bottom view of a stem portion of the atomizer assembly illustrated in FIG. 2;

FIG. 13 is a bottom view of a nasal stopper portion of the atomizer assembly illustrated in FIG. 2;

FIG. 14 is a top view of the stem illustrated in FIG. 12;

FIG. 15 is a top view of the nasal stopper illustrated in FIG. 13;

DETAILED DESCRIPTION OF THE ILLUSTRATED EMBODIMENTS

The present invention provides an apparatus and method for applying treatment fluid to facilitate certain medical procedures. Preferred embodiments are used to apply topical treatment fluid in misted form to nasal passageways.

Currently preferred fluid dispensing devices are adapted to atomize expelled treatment fluid. By "atomize expelled fluid", it is meant that the discharged fluid is dispersed substantially as a mist or cloud composed of very small droplets. Design variables incorporated in an atomizing nozzle include characteristic size of the discharge orifice, amount of pressure applied to the fluid upstream of the discharge orifice, and any turbine chamber structural arrangement to induce fluid spin. Effective atomization requires an expelled fluid to pass through a sufficient pressure drop at a discharge orifice. Further, the expelled fluid must have a rotational component of motion, (spin) about the discharge axis. Radial spread of the ejected cloud increases in correspondence with increases in the fluid spin rate at the discharge orifice.

As used in this disclosure, the term "integral" is used to mean referenced elements are formed from a single continuous piece of material. In contrast, an assembly may provide the same functionality, or even include the same elements, but is formed from more than one piece of material.

Figure 2:
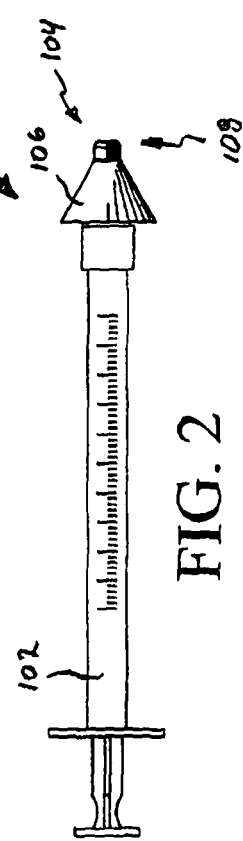
FIG. 2 is a side view, substantially to scale, of a first assembly structured according to certain principles of the invention.

A first currently preferred assembly for dispensing a treatment fluid is illustrated generally at 100 in FIG. 2. Second and third currently preferred embodiments are indicated generally at 100' and 100", respectively, in FIGS. 3 and 4. All three embodiments illustrated in FIGS. 2-4 are illustrated substantially at true scale with the attached syringes, and therefore convey a realistic sense of the visual appearance produced by such embodiments.

Figure 1:
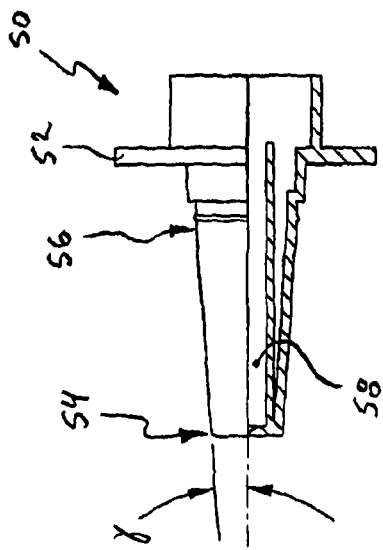
FIG. 1 is a side view, partially in section, of a commercially available actuator.

The first embodiment 100 includes a fluid motive source 102, in combination with a dispensing nozzle, generally 104. The illustrated fluid motive source 102 in FIG. 1 FIG. 2 is a 1 ml syringe, although other arrangements effective to cause pressure on a fluid are workable, including syringes having different fluid capacities. A workable 1 ml syringe may currently be obtained from Becton Dickinson at WorldWideWeb://catalog.bd.com/bdCat/viewProduct.doCustomer?productNumber=309628. It is within contemplation alternatively to supply fluid from a pressurized or pre-pressurized canister, or pump bottle, and the like.

The illustrated dispensing nozzle 104 is a 2-piece fluid atomizing nozzle operable to eject treatment fluid as a mist or cloud. Such atomizing nozzles apply spin (about an ejection axis) to a fluid just prior to ejecting the fluid through a small diameter orifice. The discharged spinning fluid experiences a significant pressure drop across the exit orifice, and is thereby effectively atomized. Dispensing nozzle 104 includes a shield 106 structured to resist over-insertion of the distal end, generally 108, into nostril openings that may have different sizes.

Figure 3:
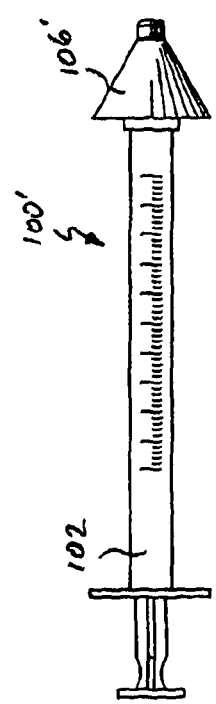
FIG. 3 is a side view, substantially to scale, of a second assembly structured according to certain principles of the invention.
Figure 4:
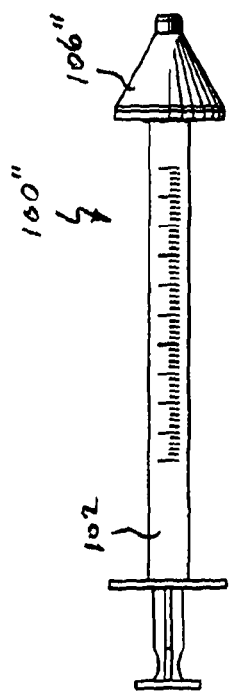
FIG. 4 is a side view, substantially to scale, of a third assembly structured according to certain principles of the invention.

First and second alternative shields 106' and 106", respectively, constitute the principal differences in structure illustrated in FIGS. 3 and 4. As illustrated, maximum sizes may be varied, as well as shape of the shields, including their trailing ends. The maximum diameter of shield 106 is 0.66 inches. The maximum diameter of shield 106' is about 0.8 inches, and the maximum diameter for shield 106" is about 0.75 inches. Currently preferred shield embodiments generally fall within such a range in maximum diameter. The trailing end of shield 106" is rounded by including a rearward projecting dogleg section. Such contouring can be more comfortable when pressed against the lip of a patient during administration of therapeutic fluids.

Figure 5:
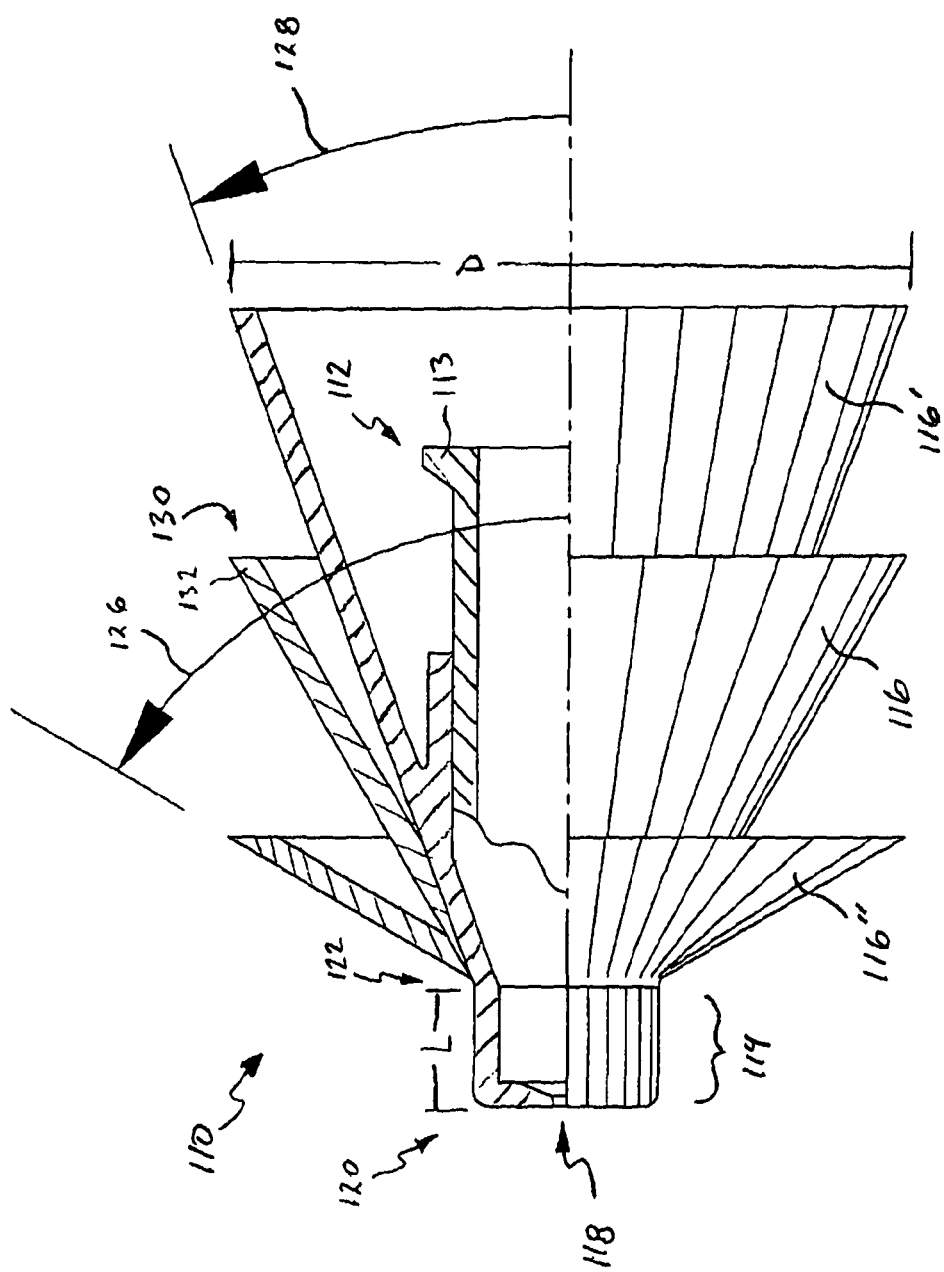
FIG. 5 is a side view, partially in section, of a superposition of a plurality of atomizing nozzles.
Figure 9:
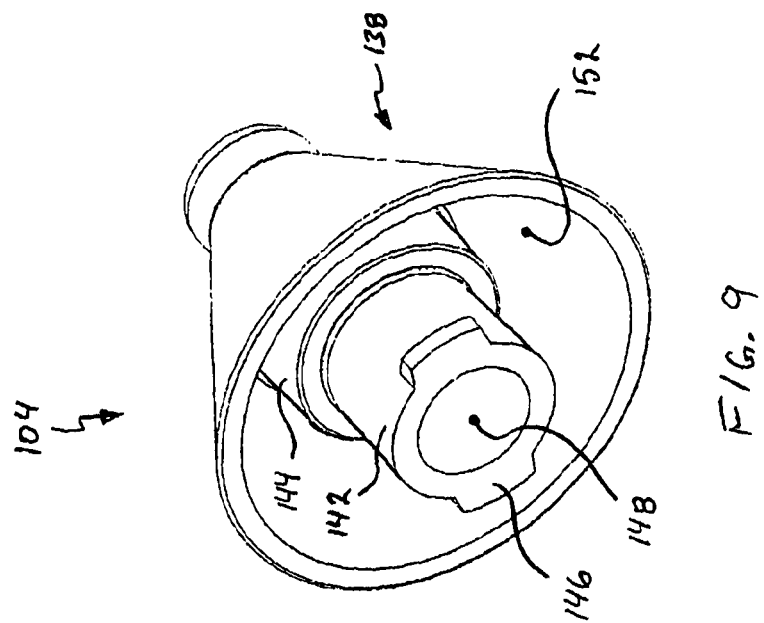
FIG. 9 is a view in perspective from below of the atomizer assembly illustrated in FIG. 2.
Figure 8:
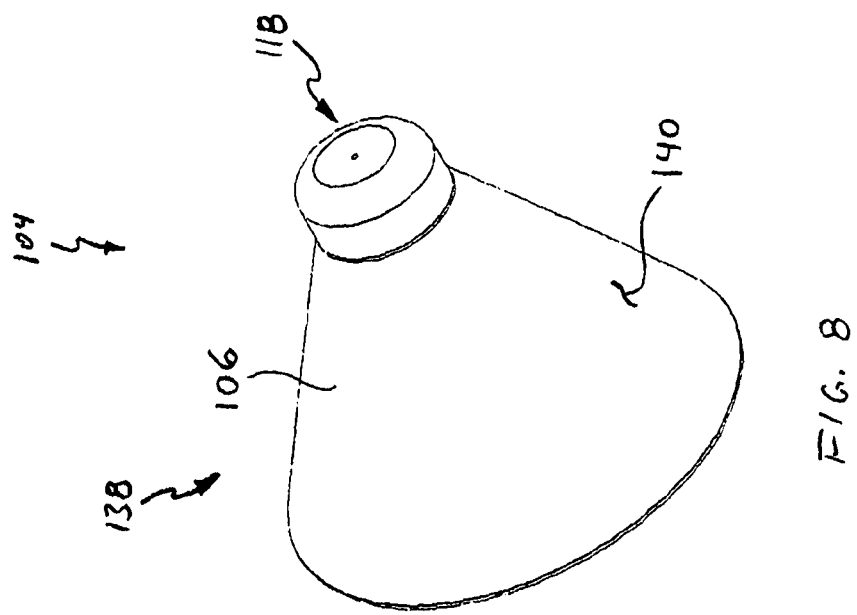
FIG. 8 is a view in perspective from above of the atomizer assembly illustrated in FIG. 2.
Figure 10:
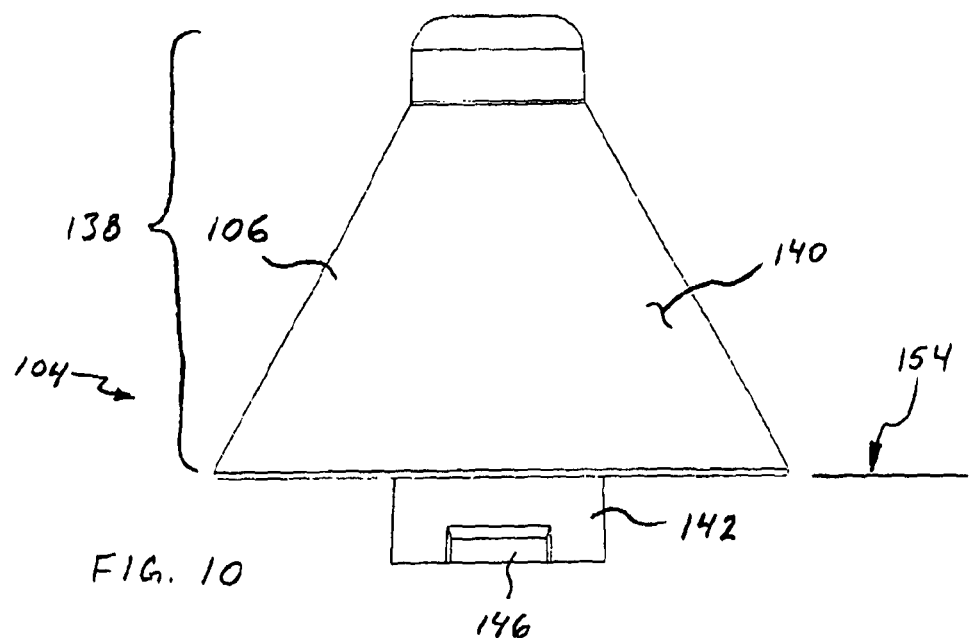
FIG. 10 is a front view of the atomizer assembly illustrated in FIG. 2.
Figure 11:
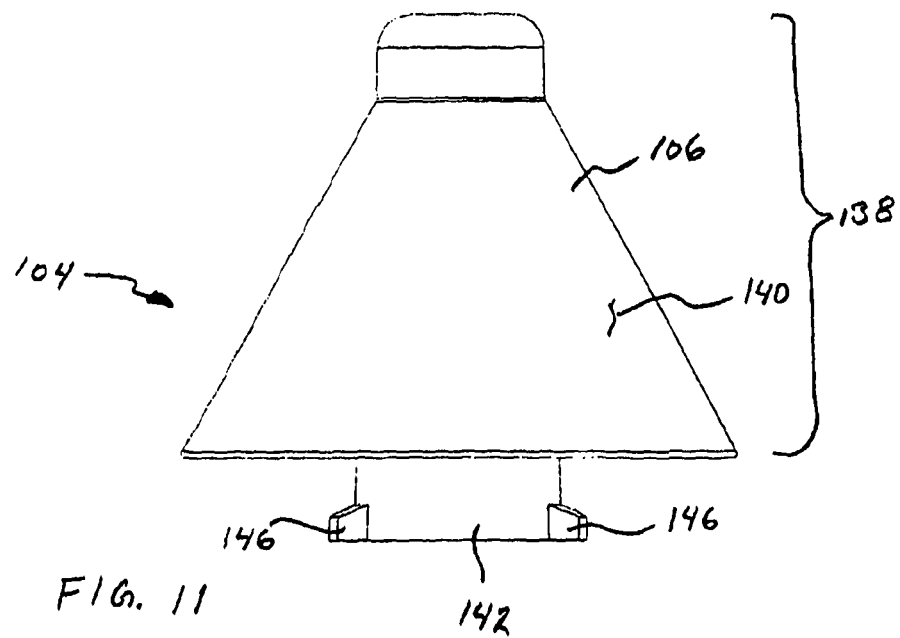
FIG. 11 is a side view of the atomizer assembly illustrated in FIG. 2.
Figure 16:
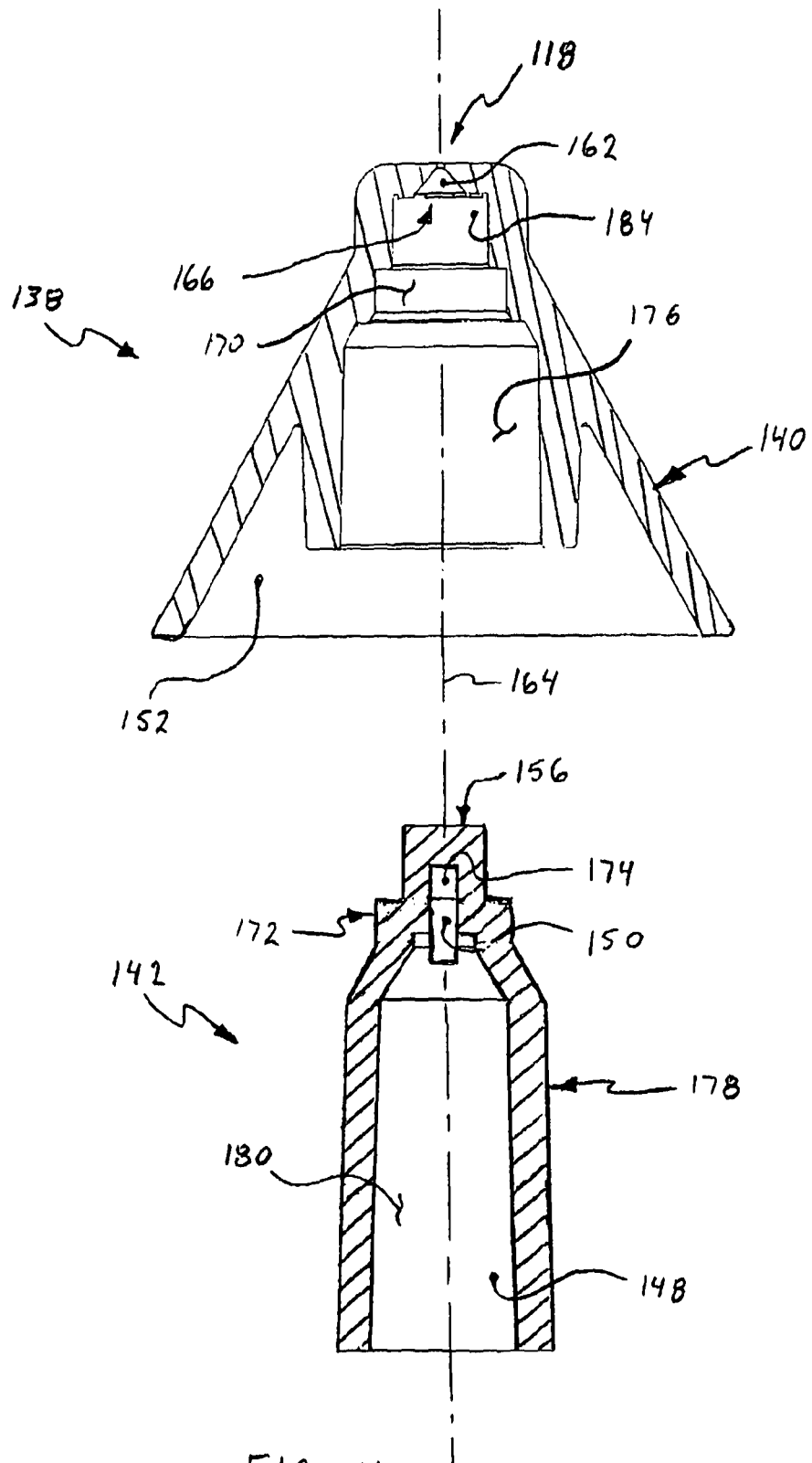
FIG. 16 is an exploded front view in cross-section of a workable 2-piece atomizer assembly structured according to certain principles of the invention.
Figure 17:
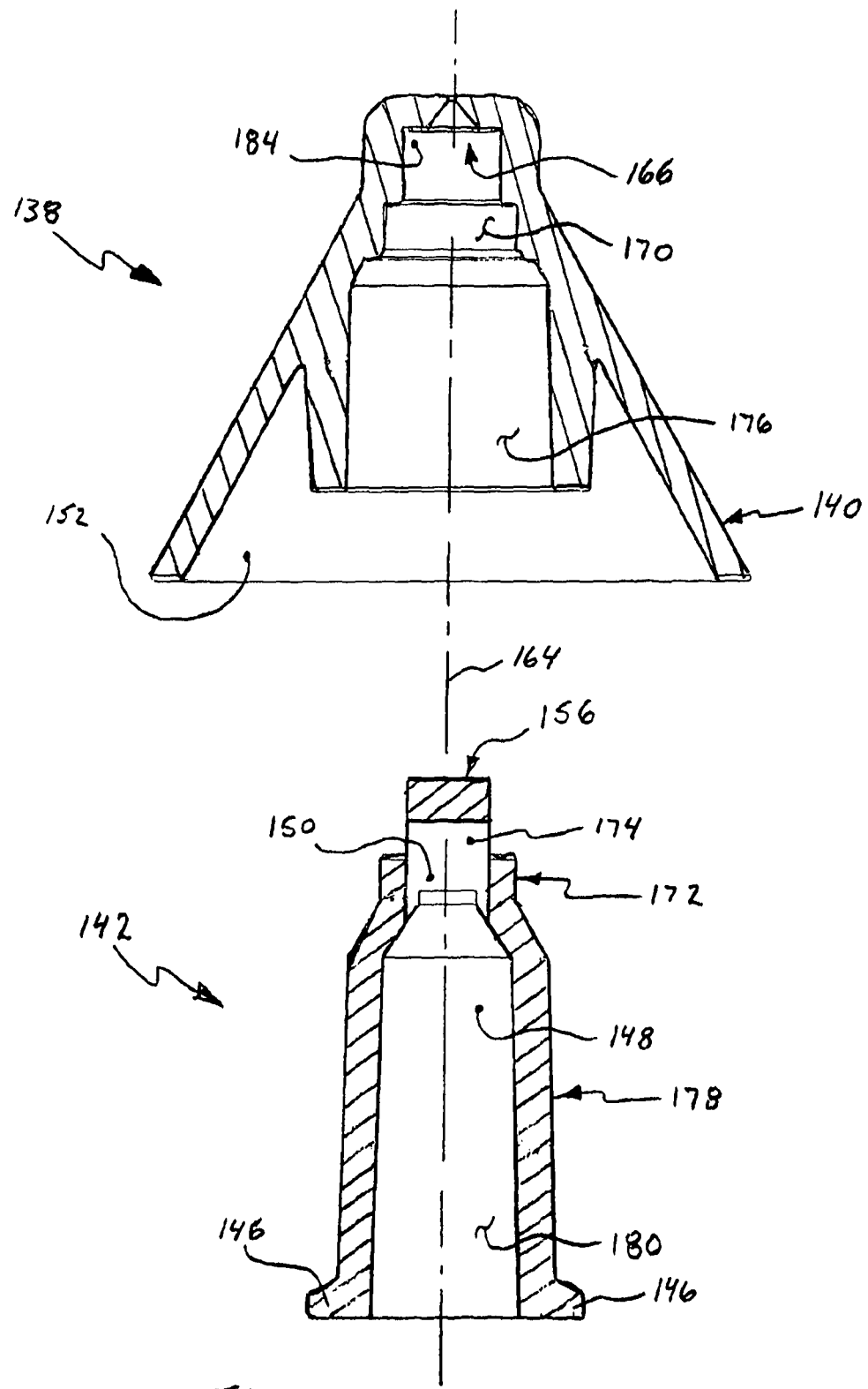
FIG. 17 is an exploded side view in cross-section of the assembly of FIG. 16.

With reference now to FIG. 5, currently preferred atomizers include a nasal stopper, generally 110, and a stem, generally 112. An exemplary stem cooperates with an exemplary nasal stopper to form an operational 2-piece atomizing nozzle. A currently preferred stem 112 carries integrated thread structure 113.

Desirably, a nasal stopper 110 includes a distally projecting tip 114, and a shield 116. The distally projecting tip 114 carries a discharge orifice, generally indicated at 118. The leading end 120 of tip 114 is desirably blunt, as illustrated, to avoid causing tissue damage inside a child's nostril. It is currently preferred for the trailing end 122 of tip 114 to be structured to suggest a cylindrical section. Furthermore, it is desirable for the cylindrical section to provide a length "L" sufficient to form a structural interference with the opening of a nostril to resist accidental transverse displacement of tip 114 from an inserted position inside that nostril. A workable length "L" is about 0.1 inches, or so. The currently preferred distally protruding tip has a length "L" of 5 mm, or about 0.13 inches. Desirably, the tip 114 is structured and sized to permit its insertion into a nostril opening of a child. That means, the diameter of the cylindrical portion of tip 114 is typically less than about 0.3 inches, with a currently preferred diameter being about 0.18 inches.

With continued reference to FIG. 5, it is preferred for a shield 116 to provide a proximal portion configured to resist over-insertion of discharge orifice 118 into a nasal opening. As illustrated, shield 116 defines a flaring wall providing a variable diameter sized to contact skin around the opening of a plurality of different-sized nostrils, Although other shapes are workable, illustrated shield 116 presents a substantially conic surface for contact with a nostril opening area, Desirably, a shield is structured to provide a measure of centering and orienting to facilitate positioning discharge orifice 118 in a nasal cavity. While even a flat washer is workable, it should be realized that a too shallow conic angle permits over-insertion, and a too steep conic angle starts to loose self-centering ability, A workable conic angle may be selected from a range between a minimum value 128 of about 20 degrees (see shield 116'), and a maximum value 126 of about 60 degrees (see shield 116"), The currently preferred shield 116 in FIG. 5 has a conic angle of 30 degrees and a maximum diameter "D" at proximal end 130 of about 0.66 inches.

Figure 1A:
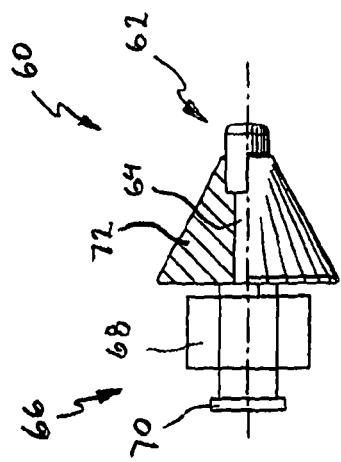
FIG. 1A is a side view, partially in section, of a commercially available atomizing nozzle assembly adapted for nasal therapy.

A preferred shield, such as shield 116 in FIG. 5, presents a smooth contact surface, which is devoid of radial protrusions, to the nostril and lip areas of a patient. Desirably, the contact surface is structured to make a seal against skin at the nostril opening. Also, it is preferred to structure a shield to provide a self-centering capability to urge a discharge orifice away from a nasal wall. The illustrated contact surface is formed by revolving a shape about a centerline. Such a smooth contact surface is in contrast to the oblong transverse trigger structure illustrated in FIG. 1. Further, the proximal end of a preferred contact surface is structured as a shell to provide an open cantilevered free end 132. Such cantilevered structure 132 is in contrast to the solid proximal surface of stopper 72 illustrated in FIG. 1A.

It is realized that humans are variable in their sizes and conformation. For purpose of this disclosure, it will be assumed that a nostril opening of a human child is less than 0.3 inches in diameter. The dispensing tip of the atomizer illustrated in FIG. 1 simply cannot fit into a nostril of that child. In practice, a clinician places the dispensing end against the child's nasal opening, and hopes for sufficient alignment of the discharge orifice and nostril opening. One aspect of certain preferred embodiments of a nasal stopper 110 provides a protruding distal tip sized for reception inside the nostril of a child. Desirably, proximal shield structure of the nasal stopper is configured to resist over-insertion of the protruding tip in the nostril of a child, as well as a large number of adults. It is recognized that certain adult nostrils may be sufficiently large that preferred nasal stoppers may not provide self-centering or seal against skin at the nasal opening. However, the currently preferred nasal stoppers are believed to work well with the vast majority of human nostrils.

FIGS. 6-11 illustrate externally visible details of the atomizing nozzle assembly 104 illustrated in FIG. 2. Such FIGS. are illustrated in true scale, and therefore convey a realistic sense of the visual appearance produced by a currently preferred atomizer for nasal therapy. Nasal stopper 138 includes shield 106 with contact surface 140 configured to form a seal against skin at the nostril opening of a nostril selected from a plurality of nostrils having different sizes. Stem 142 couples with nasal stopper 138 to form a workable 2-piece atomizer assembly. As best illustrated in FIG. 9, stem 142 is received in standoff 144. Integral thread structure, such as a plurality of thread lugs 146, is carried at a proximal end of stem 142. It is within contemplation to extend alternative thread structure around a circumference of stem 142. A 6% bore 148 is provided inside stem 142 to couple with the dispensing tip of a syringe and to conduct treatment fluid toward throat 150 for eventual discharge through discharge orifice 118. A volume 152 is defined by proximally open-ended skirt-like cantilevered shell structure of shield 106. One boundary of such volume is provided by plane 154 defined by structure at the proximal end of shield 106.

Figure 20:
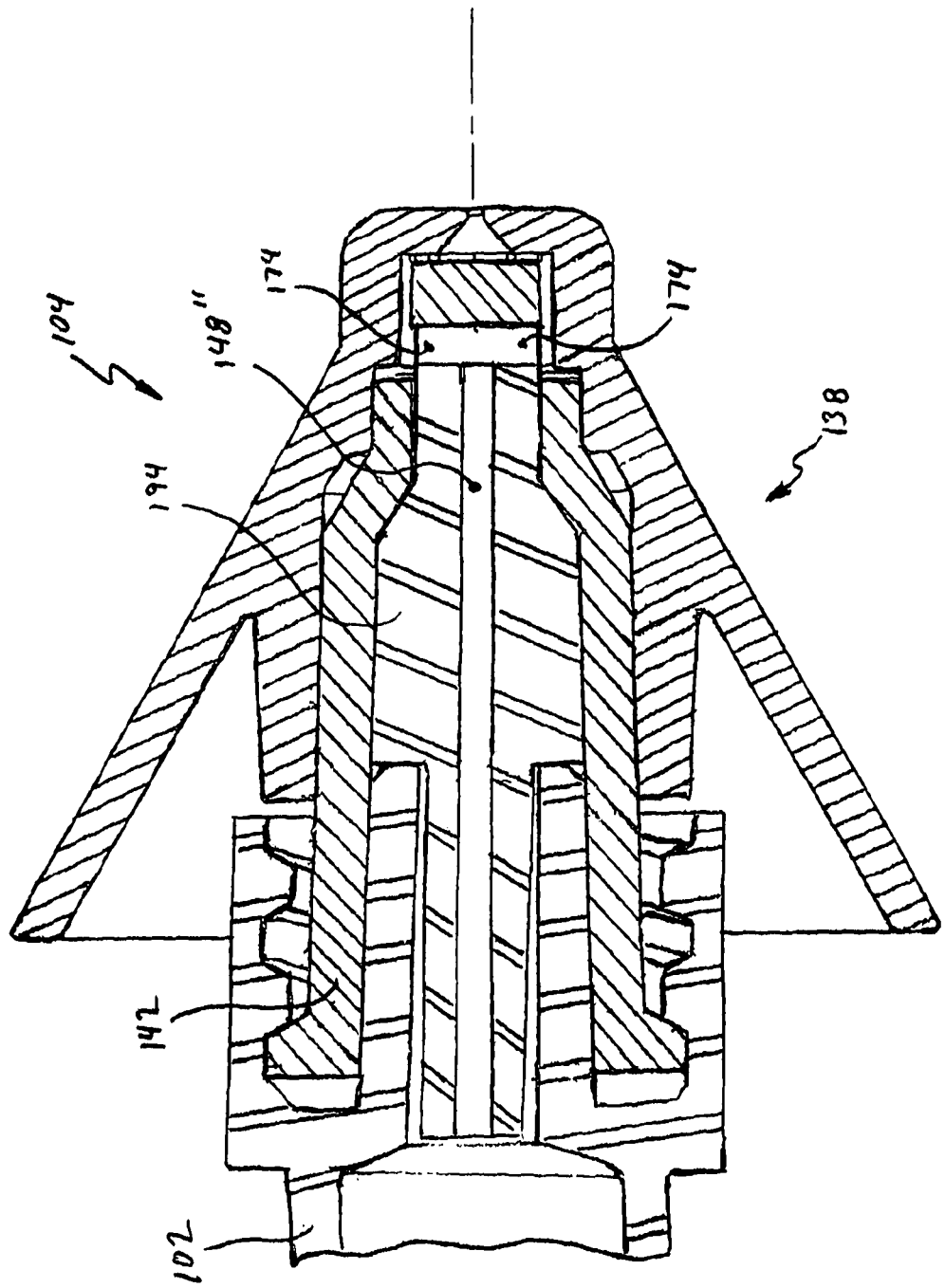
FIG. 20 is a view similar to FIG. 19, including alternative spacing structure to reduce dead volume inside the atomizer assembly and syringe.

FIGS. 12-15 illustrate certain cooperating internal structure of atomizing assembly 104. With reference to FIG. 12, a distal end of stem 142 is configured to form anvil surface 156. With reference to FIG. 15, anvil surface 156 is assembled to press against standoff surfaces 158, thereby defining a plurality of substantially fluid-tight turbine blades 160. Thus, fluid introduced through throat 150 is caused to pass through turbine blades 160 and subsequently enter turbine chamber 162. Fluid in turbine chamber 162 acquires a spin prior to being expelled through discharge orifice 118.

With reference to FIG. 16, it can be visualized that anvil surfaces 156 is advanced along central axis 164 until that distal surface 156 encounters the cooperating proximal surface(s) of turbine structure, generally indicated at 166, disposed around a perimeter of conic turbine chamber 162. Turbine structure 166 includes a plurality of standoff surfaces 158 and turbine blades 160 best illustrated in FIG. 15. Therefore, anvil surface 156 forms a portion of a proximal wall of turbine chamber 162.

In the embodiment illustrated in FIGS. 16-18, a primary fluid seal is formed between internal surface 170 of nasal stopper 138 and cooperating external surface 172 of stem 142. Desirably, the primary fluid seal is disposed in close proximity to the one or more (two are illustrated) side discharge opening 174 disposed near the distal end of stem 142. A side discharge opening 174 provides a portion of the fluid path extending through stem 142 and causes a transverse component of velocity in fluid flowing there-through. Of note, the transverse component of travel is enforced at a location inside the fluid supply lumen and proximal to the distal end of stem 142. In other words, a preferred stem is structured to require fluid to discharge in a radial direction from at least one side discharge opening disposed at a location proximal to the distal end of that stem.

A primary torsion-transfer coupling is created between internal surface 176 of nasal stopper 138 and a cooperating external surface 178 of stem 142. The contact area of the illustrated torsion-transfer coupling is larger than the contact area of the primary fluid seal. Further, the radius extending to the torsion-carrying coupling is larger than the radius extending to the primary fluid seal surface. Therefore, the primary torsion-transfer coupling carries more torsion loading than the primary fluid seal surface. The cooperating elements that form a workable torsion-transfer coupling permit a user to grasp the contact surface 140 and impart twist to a nasal stopper 138 effective to install, and to remove, an atomizer onto luer-locking structure of a syringe, such as included at the distal end of syringe 102 in FIG. 18.

The primary fluid seal can operate as a secondary torsion-transfer coupling. Also, the primary torsion-transfer coupling may function as a secondary fluid seal. It is currently preferred for both of the primary fluid seal and the primary torsion-coupling to be caused by an interference, or press-fit, between the cooperating elements. However, it is within contemplation that one or more such junction may be formed by alternative means, including adhesive joints, and the like. Also, it is within contemplation alternatively to provide a single surface at which to form a combined fluid seal and torsion-carrying coupling.

With reference now to FIG. 18 (in which the syringe is not entirely to scale), the discharge end of a syringe 102 is conventionally jammed into compression against surface 180 of 6% bore 148 during engagement of cooperating luer-locking structure of syringe 102 and stem 142. Such an arrangement forms a fluid-tight coupling between the syringe 102 and stem 142. Treatment fluid flows from discharge bore 182, along unoccupied portion of the 6% bore 148, through throat 150, exits stem 142 through one or more side discharge opening 174, and then flows into liquid zone 184. The illustrated liquid zone 184 is essentially a cylindrical annulus about 0.015 inches in thickness and extending along axis 164 for a distance of about 0.1 inches. Fluid in liquid zone 184 is already displaced in a radial direction from the centerline axis 164 and enters openings of one or more turbine blade 160 (see FIG. 15). Fluid exits a turbine blade 160 into turbine chamber 162 with a spin. If sufficiently pressurized, fluid is then ejected through discharge orifice 118 as a mist.

With continued reference to FIG. 18, a dead volume may be defined as the volume of fluid remaining in a fluid transporting device subsequent to exhaustion of operable fluid pumping. Such dead volume for atomizer 104 includes the working portion (or portion unoccupied by syringe or other pumping device) of the 6% bore 148, throat 150, any side discharge openings 174, liquid zone 184, turbine blade(s) 160, and turbine chamber 162. The dead volume for a syringe 102 having a conventional plunger includes primarily the bore 182. The dead volume for the exemplary assembly 102/104 illustrated in FIG. 18 has been calculated to be about 0.102 ml, about half of which is contained in the syringe 102, and half in the atomizer 104. It is often desirable to minimize the dead volume, e.g. to reduce waste of treatment fluid when dispensing a single dose and subsequently discarding the dispensing device.

One way to reduce dead volume in an atomizer assembly similar to assembly 104 is to reduce the length of the primary torsion-transfer coupling area, and neck down the distal portion of the 6% bore 148. However, because it is possible to generate 600 psi with a 1 ml syringe 102, there is some danger of separation of a press-fit stem 142 from a nasal stopper 138 if the contact area is excessively reduced.

An alternative approach to reduce dead volume in an atomizer, such as atomizer assembly 104, is illustrated in FIG. 19. A volume-reducing insert 190 may be installed in bore 148 and throat 150 to displace a substantial portion of dead volume within the atomizer 104. The lumen 148' essentially replaces the fluid conducting path previously provided by the unoccupied portion of the 6% bore 148 and throat 150, which constitutes the majority of the dead volume of an atomizer assembly 104. The remaining dead volume in the combination illustrated in FIG. 19 is less than about 0.07 ml. Preferred embodiments of the atomizer nozzle assembly, itself, provide a small dead volume; including a dead volume of less than about 0.03 ml, less than about 0.02 ml, and even less than about 0.01 ml. The illustrated atomizer assembly 104 and insert 190 would have a dead volume of easily less than about 0.02 ml when used in combination with a syringe having a plunger configured to cause essentially zero dead volume within the syringe.

A further reduction in dead volume of an assembly including a syringe 102 and atomizer assembly 104 may be effected by an arrangement such as illustrated in FIG. 20. Volume-reducing insert 194 is installed in bore 148 and throat 150, and also projects proximally into bore 182 to displace a substantial portion of dead volume in the assembly formed by syringe 102 and atomizer 104. The lumen 148" essentially replaces the fluid conducting path previously provided by bore 182, the unoccupied portion of the 6% bore 148, and throat 150, which cause the majority of the dead volume of an assembly including syringe 102 and atomizer 104. The remaining dead volume in the illustrated embodiment in FIG. 20 is in the ballpark of about 0.02 ml. Preferred embodiments of an assembled combination of a nasal atomizing nozzle and syringe provide a small dead volume; including a dead volume of less than about 0.03 ml, less than about 0.02 ml, and even less than about 0.01 ml.

Figure 21:
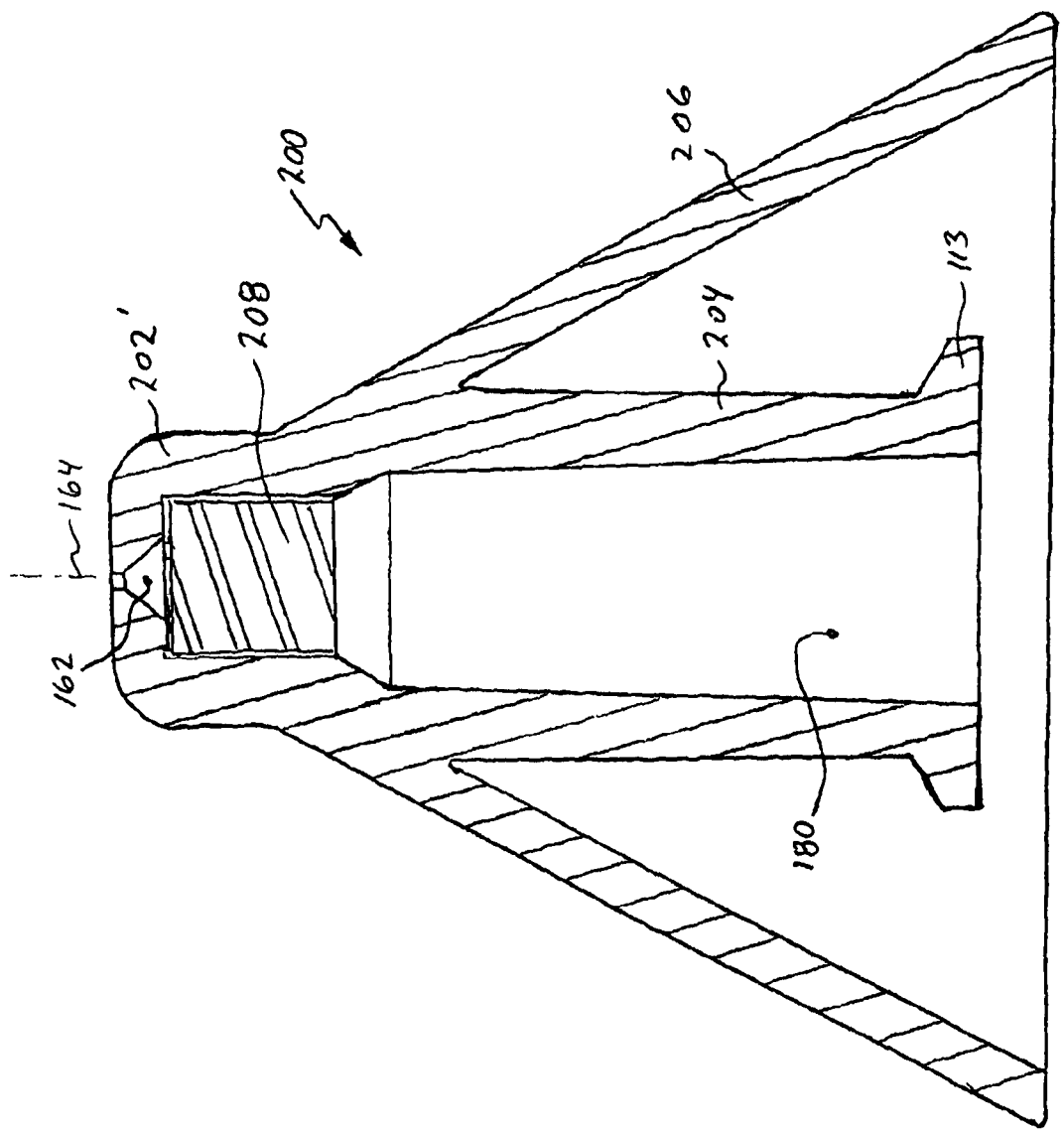
FIG. 21 is a side view in cross-section of a workable 2-piece atomizer structured according to certain principles of the invention.

FIG. 21 illustrates another embodiment of a 2-piece atomizer, generally indicated at 200, structured according to certain principles of the invention. Atomizer 200 includes an integral protruding distal tip 202', integral stem 204, and integral shield 206. The integrated structure of the atomizer can require rather specialized tooling to manufacture by way of currently preferred injection molding. However, certain of such tooling permits integrated thread structure 113 to even be disposed within the volume defined by distally open-ended shield 206, as illustrated.

Figure 18:
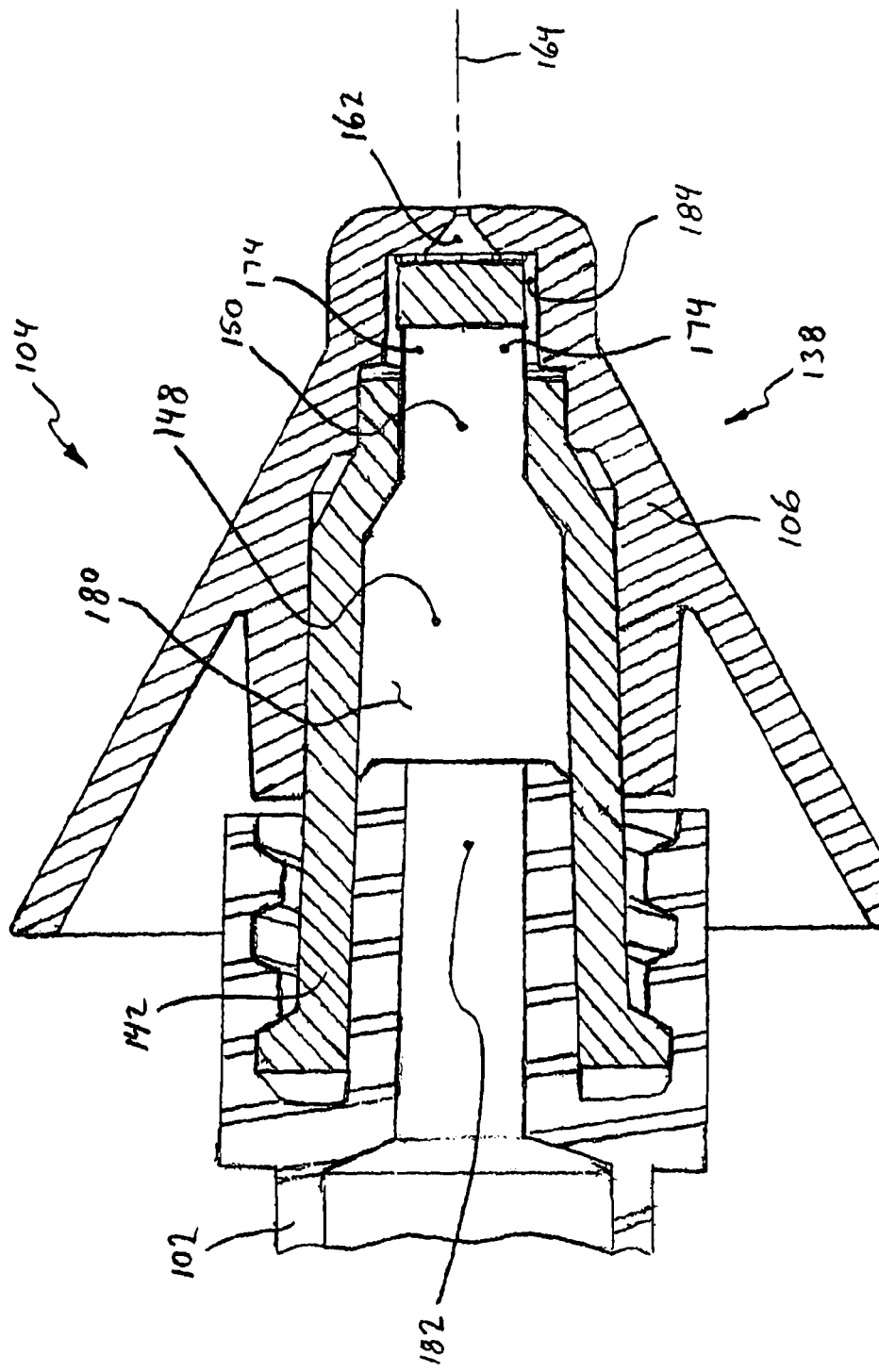
FIG. 18 is an assembled view of the structure illustrated in FIG. 17, installed on a syringe.
Figure 19:
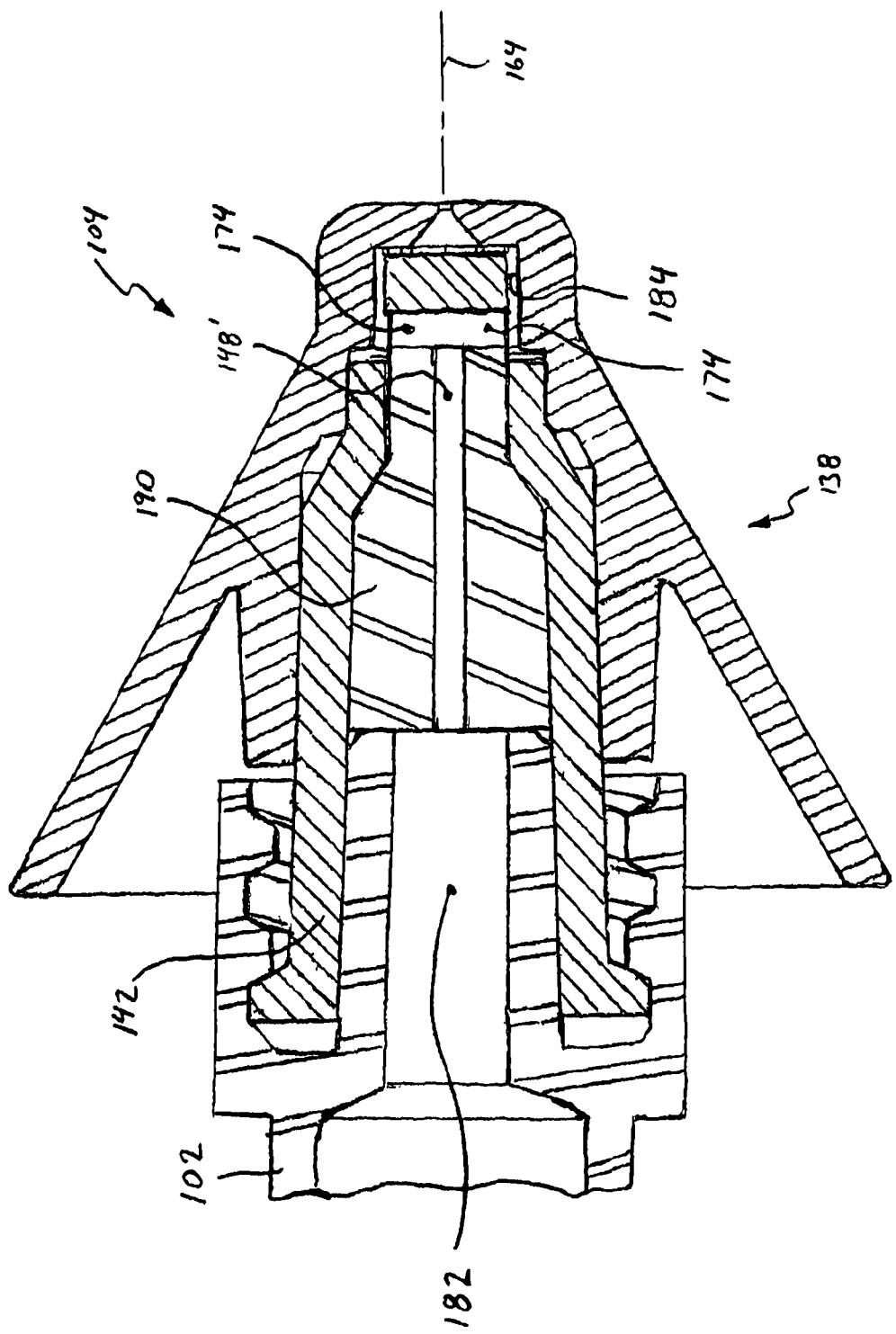
FIG. 19 is a view similar to FIG. 18, including alternative spacing structure to reduce dead volume inside the atomizer assembly.
Figure 22:
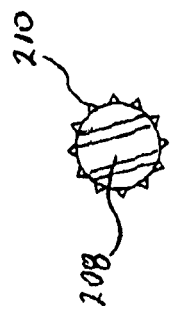
FIG. 22 is a cross-section view of the fluid guidance structure illustrated in FIG. 21.

Workable turbine structure carried internal to distal tip 202' is equivalent to the turbine structure 166 in FIG. 15. Fluid guidance structure 208 provides the same functionality as the distal end of a stem 142, and distributes treatment fluid toward a liquid zone 184 (e.g. see FIG. 18). One workable fluid guidance structure 208 is shown in cross-section in FIG. 22. The illustrated fluid guidance structure 208 may be manufactured by cutting a length of extruded material to a desired length. The guidance structure 208 may then be installed by press-fitting the cut length into an installed position. In such case, an outer radial dimension of ribs 210 is sized to cause a suitable press-fit engagement within the distal end of bore 180. Treatment fluid can then flow in the direction of central axis 164 between adjacent ribs 210 of an installed fluid guidance structure 208 and enter turbine chamber 162 by way of one or more turbine blade. The distal surface of guidance structure 208 forms an anvil surface equivalent to the anvil surface 156 of stem 142. If desired, a volume-reducing insert (e.g. structured similar to insert 190 in FIG. 19), may be installed to reduce dead volume inside an atomizer 200.

It is currently preferred to manufacture elements such as a stem, stopper, and spacer, by injection molding. A workable stem and/or stopper element is typically made from medical grade plastics, such as ABS, polypropylene, and polycarbonate. A workable spacer may be made from similar materials, or more compliant materials, such as rubber, urethane, and the like. Preferred assembly of a separate, or non-integral, stem to a stopper is accomplished with a press-fit joint between the elements. A radial interference of about 0.001 or 0.002 inches is workable to form a torsion-transfer coupling in polycarbonate elements structured similar to the embodiment illustrated in FIG. 18. For similar elements made from polypropylene, the radial interference should be increased to about 0.004 inches. In alternative construction, an adhesive joint may be used to joint a stem to a stopper. Workable adhesives are well known, and may be selected as appropriate for the material of composition of respective elements. For example, polycarbonate materials may be bonded with cyclohexanone solvent adhesive. UV-curing adhesives may be used in some cases. Preferably, a spacer is installed in a bore of an atomizer using a press-fit.

After having been apprised of the instant disclosure, one of ordinary skill in the art will be readily able to make the disclosed structure using commercially available materials and tools.

What is claimed is:

1. An apparatus comprising:
    a fluid discharge orifice defined in a distal end of a nasal stopper, a proximal portion of the nasal stopper comprising a shield configured to resist over-insertion of the discharge orifice into a nostril opening, the shield comprising a frustoconical surface; a proximal end of the frustoconical surface being configured as a cantilevered free end; and
    a stem structured to provide a lumen for communication of treatment fluid to a turbine chamber for discharge of an atomized fluid from the discharge orifice, the stem extending in a length direction between a proximal end and a distal end, the nasal stopper being affixed to the distal end of the stem;
    wherein a thread structure carried at the proximal end of the stem is configured to couple with a luer-locking portion of a syringe;
    wherein the combination of the stem assembled to the nasal stopper is operable as an atomizing nozzle, the atomizing nozzle comprising the discharge orifice, the discharge orifice being disposed in a wetted fluid path to conduct fluid from the turbine chamber;
    wherein a first cooperating coupling structure configured between a first external surface of the stem and a first internal surface of the nasal stopper forms a distal fluid seal to resist leakage of fluid from the lumen;
    wherein a second cooperating coupling structure configured between a second external surface of the stem and a second internal surface of the nasal stopper forms a torsion-carrying connection between said stem and nasal stopper;
    wherein the stem is configured to couple with the nasal stopper; and
    wherein a portion of a proximal wall of the turbine chamber is disposed at a distal end of the stem to assist in discharge of the treatment fluid in atomized form.

2. The apparatus of claim 1, wherein:
    the stem is sized in length such that, upon assembly of the apparatus, the thread structure is disposed inside an interior volume defined by the nasal stopper.

3. The apparatus of claim 1, wherein:
    the stem consists of a single unitary element;
    the nasal stopper consists of a single unitary element; and
    the combination consisting of the stem and the nasal stopper is operable as the atomizing nozzle.

4. The apparatus of claim 1, wherein the nasal stopper is configured to define:
    a distally projecting tip carrying the discharge orifice, the distally projecting tip being structured and sized to permit insertion of the distally projecting tip into the nostril opening, a leading end of the distally projecting tip being blunt to avoid causing tissue damage inside a nostril, a trailing end of the tip being structured as a cylindrical section, a diameter of the cylindrical section being sized to form an interference with structure of the nostril to resist transverse displacement of the distally projecting tip from an inserted position inside the nostril; and
    wherein the shield is affixed to the distally projecting tip and arranged to define a flaring wall providing a variable diameter sized to contact skin around the opening of a plurality of different-sized nostrils effective to resist the over-insertion.

5. The apparatus of claim 4, wherein:
    the shield has a longitudinal axis and the frustoconical surface defines conic angle, and the conic angle is selected from the range of between 20 degrees and 60 degrees taken from said longitudinal axis.

6. The apparatus of claim 5, wherein the conic angle is 30 degrees.

7. The apparatus of claim 1, wherein:
the stem is structured to require fluid to discharge in a radial direction from at least one side discharge opening disposed at a location proximate to the distal end of the stem.

8. The apparatus of claim 1, wherein:
a portion of the proximal wall of the turbine chamber is defined by a fluid guidance structure comprising a proximally oriented anvil surface disposed in contact with a standoff structure of the turbine chamber, and
the fluid guidance structure is configured and arranged to form a press-fit within cooperating lumen structure of the stem.

9. An apparatus comprising:
a stem consisting of a single unitary element and comprising a lumen extending from a proximal end toward a distal end, the proximal end including thread structure capable of coupling with luer-locking structure of a syringe; and
a nasal stopper having a proximal portion comprising a shield comprising a frustoconical surface and configured to resist over-insertion of the apparatus into a nostril opening, said nasal stopper consisting of a single unitary element, the nasal stopper being affixed to the distal end of the stem;
wherein the combination consisting of the stem assembled to the nasal stopper is operable as an atomizing nozzle;
wherein a first cooperating coupling structure configured between a first external surface of the stem and a first internal surface of the nasal stopper forms a distal fluid seal to resist leakage of fluid from the lumen;
wherein a second cooperating coupling structure configured between a second external surface of the stem and a second internal surface of the nasal stopper forms a torsion-carrying connection between said stem and nasal stopper;
wherein the stem is configured to couple with the nasal stopper; and
wherein a portion of a proximal wall of a turbine chamber is disposed at a distal end of the stem to assist in discharge of the treatment fluid in atomized form.

10. The apparatus of claim 9, wherein the nasal stopper comprises structure arranged to permit insertion of a distal end of the nasal stopper into the nostril opening of a human child, and to resist over-insertion of the distal end of the apparatus into the opening.

11. The apparatus of claim 9, wherein:
the stem is sized in length such that, upon assembly of the apparatus, the thread structure is disposed inside an interior volume defined by the nasal stopper.

12. The apparatus of claim 9, wherein:
the stem is structured to require fluid to discharge from the lumen in a radial direction at a location proximate to the distal end of the stem.

13. An apparatus comprising:
a stem consisting of a single unitary element and comprising a lumen extending from a proximal end toward a distal end, the proximal end including thread structure able to couple with luer-locking structure of a syringe;
a turbine chamber defined within the apparatus, the turbine chamber being in fluid communication with the lumen of the stem;
a nasal stopper configured to couple with the stem and affixed to the distal end of the stem, said nasal stopper having a proximal portion comprising a shield comprising a frustoconical surface, wherein the shield has a longitudinal axis and the frustoconical surface defines a conic angle, the conic angle being selected from a range of between 20 degrees and 60 degrees taken from the longitudinal axis, and wherein the shield is configured to resist over-insertion of the apparatus into a nostril opening, the nasal stopper consisting of a single unitary element; and
wherein the combination consisting of the stem assembled to the nasal stopper is operable as an atomizing nozzle;
wherein a first cooperating coupling structure configured between a first external surface of the stem and a first internal surface of the nasal stopper forms a distal fluid seal to resist leakage of fluid from the lumen;
wherein a second cooperating coupling structure configured between a second external surface of the stem and a second internal surface of the nasal stopper forms a torsion-carrying connection between said stem and nasal stopper; and
wherein a portion of a proximal wall of the turbine chamber is disposed at a distal end of the stem to assist in discharge of the treatment fluid in misted or atomized form from the apparatus.

* * * * *